(12) United States Patent
Monk et al.

(10) Patent No.: US 8,756,437 B2
(45) Date of Patent: Jun. 17, 2014

(54) SYSTEM AND METHOD OF ENCRYPTION FOR DICOM VOLUMES

(75) Inventors: David Monk, Mission Viejo, CA (US); John C. Canessa, Apple Valley, MN (US); Giancarlo Canessa, Rosemount, MN (US); Gino G. Canessa, Eagan, MN (US)

(73) Assignee: Datcard Systems, Inc., Irvine, CA (US)

( * ) Notice: Subject to any disclaimer, the term of this patent is extended or adjusted under 35 U.S.C. 154(b) by 1189 days.

(21) Appl. No.: 12/546,611

(22) Filed: Aug. 24, 2009

(65) Prior Publication Data

US 2010/0115288 A1    May 6, 2010

Related U.S. Application Data

(60) Provisional application No. 61/091,161, filed on Aug. 22, 2008, provisional application No. 61/119,012, filed on Dec. 1, 2008.

(51) Int. Cl.
G06F 21/24        (2006.01)
(52) U.S. Cl.
USPC .............. 713/193; 713/165; 713/166; 380/44
(58) Field of Classification Search
USPC .............................. 713/193, 166, 165; 380/44
See application file for complete search history.

(56) References Cited

U.S. PATENT DOCUMENTS

| | | | |
|---|---|---|---|
| 4,149,239 A | 4/1979 | Jenkins et al. | |
| 4,386,233 A | 5/1983 | Smid et al. | |
| 4,491,725 A | 1/1985 | Pritchard | |
| 4,852,570 A | 8/1989 | Levine | |
| 4,860,112 A | 8/1989 | Nichols | |
| 4,874,935 A | 10/1989 | Younger | |
| 4,945,410 A | 7/1990 | Walling | |
| 4,958,283 A | 9/1990 | Tawara et al. | |
| 5,002,062 A | 3/1991 | Suzuki | |

(Continued)

FOREIGN PATENT DOCUMENTS

| | | |
|---|---|---|
| DE | 19802572 | 5/1999 |
| EP | 0684565 | 11/1995 |

(Continued)

OTHER PUBLICATIONS

The International Search Report, PCT/US2009/054799, dated Mar. 3, 2011.

(Continued)

Primary Examiner — Jung Kim
Assistant Examiner — Thomas Ho
(74) Attorney, Agent, or Firm — Knobbe, Martens, Olson & Bear LLP

(57) ABSTRACT

Digital image storage and management systems capable of producing encrypted DICOM volumes on different types of media (e.g., Blu-ray, CD, DVD, memory stick, USB flash drive, etc.), with or without the automatic generation of labels, systems and mechanisms to generate and manage passwords for the encrypted volumes, and systems and mechanisms to manage access to encrypted data on such volumes are disclosed. Generated encrypted DICOM volumes, which can comprise confidential patient data, can be securely interchanged, archived, and distributed to users. The disclosed systems and methods can permit authorized users to access encrypted data, even if the users do not have access to the original encryption mechanism. Encrypted data stored on the volume can be easily and securely accessed by a variety of authorized users.

6 Claims, 9 Drawing Sheets

(56) References Cited

U.S. PATENT DOCUMENTS

| | | |
|---|---|---|
| 5,005,126 A | 4/1991 | Haskin |
| 5,019,975 A | 5/1991 | Mukai |
| 5,208,802 A | 5/1993 | Suzuki |
| 5,235,510 A | 8/1993 | Yamada et al. |
| 5,272,625 A | 12/1993 | Nishihara et al. |
| 5,291,399 A | 3/1994 | Chaco |
| 5,319,543 A | 6/1994 | Wilhelm |
| 5,319,629 A | 6/1994 | Henshaw et al. |
| 5,321,520 A | 6/1994 | Inga et al. |
| 5,321,681 A | 6/1994 | Ramsay et al. |
| 5,384,643 A | 1/1995 | Inga et al. |
| 5,410,676 A | 4/1995 | Huang et al. |
| 5,416,602 A | 5/1995 | Inga et al. |
| 5,451,763 A | 9/1995 | Pickett et al. |
| 5,469,353 A | 11/1995 | Pinsky et al. |
| 5,499,293 A | 3/1996 | Behram et al. |
| 5,513,101 A | 4/1996 | Pinsky et al. |
| 5,531,227 A | 7/1996 | Schneider |
| 5,541,994 A * | 7/1996 | Tomko et al. .................. 380/30 |
| 5,542,768 A | 8/1996 | Rother |
| 5,544,649 A | 8/1996 | David et al. |
| 5,559,888 A | 9/1996 | Jain et al. |
| 5,586,262 A | 12/1996 | Komatsu et al. |
| 5,597,182 A | 1/1997 | Reber |
| 5,597,995 A | 1/1997 | Williams |
| 5,605,153 A | 2/1997 | Fujioka et al. |
| 5,655,084 A | 8/1997 | Pinsky et al. |
| 5,659,741 A | 8/1997 | Eberhardt |
| 5,671,353 A | 9/1997 | Tian et al. |
| 5,687,717 A | 11/1997 | Halpern et al. |
| 5,721,825 A | 2/1998 | Lawson et al. |
| 5,724,582 A | 3/1998 | Pelanek et al. |
| 5,734,629 A | 3/1998 | Lee |
| 5,734,915 A | 3/1998 | Roewer |
| 5,763,862 A | 6/1998 | Jachimowicz |
| 5,784,460 A * | 7/1998 | Blumenthal et al. ............ 705/51 |
| 5,796,862 A | 8/1998 | Pawlicki et al. |
| 5,809,243 A | 9/1998 | Rostoker |
| 5,822,544 A | 10/1998 | Chaco et al. |
| 5,823,948 A | 10/1998 | Ross et al. |
| 5,832,488 A | 11/1998 | Eberhardt |
| 5,848,198 A | 12/1998 | Penn |
| 5,848,435 A | 12/1998 | Brant et al. |
| 5,859,628 A | 1/1999 | Ross et al. |
| 5,867,795 A | 2/1999 | Novis et al. |
| 5,867,821 A | 2/1999 | Ballantyne et al. |
| 5,869,163 A | 2/1999 | Smith et al. |
| 5,873,824 A | 2/1999 | Doi et al. |
| 5,882,555 A | 3/1999 | Rohde et al. |
| 5,884,271 A | 3/1999 | Pitroda |
| 5,899,998 A | 5/1999 | McGauley et al. |
| 5,909,551 A | 6/1999 | Tahara et al. |
| 5,911,687 A | 6/1999 | Sato et al. |
| 5,914,918 A | 6/1999 | Lee et al. |
| 5,924,074 A | 7/1999 | Evans |
| 5,942,165 A | 8/1999 | Sabatini |
| 5,946,276 A | 8/1999 | Ridges |
| 5,950,207 A | 9/1999 | Mortimore |
| 5,982,736 A | 11/1999 | Pierson |
| 5,995,077 A | 11/1999 | Wilcox |
| 5,995,345 A | 11/1999 | Overbo |
| 5,995,965 A | 11/1999 | Experton |
| 6,006,191 A | 12/1999 | DiRienzo |
| 6,014,629 A | 1/2000 | DeBruin-Ashton |
| 6,021,404 A | 2/2000 | Moukheibir |
| 6,022,315 A | 2/2000 | Iliff |
| 6,032,120 A | 2/2000 | Rock et al. |
| 6,041,703 A | 3/2000 | Salisbury et al. |
| 6,067,075 A | 5/2000 | Pelanek |
| 6,131,090 A | 10/2000 | Basso, Jr. et al. |
| 6,148,331 A | 11/2000 | Parry |
| 6,149,440 A | 11/2000 | Clark et al. |
| 6,155,409 A | 12/2000 | Hettinger |
| 6,241,668 B1 | 6/2001 | Herzog |
| 6,260,021 B1 | 7/2001 | Wong et al. |
| 6,272,470 B1 | 8/2001 | Teshima |
| 6,278,999 B1 | 8/2001 | Knapp |
| 6,283,761 B1 | 9/2001 | Joao |
| 6,363,392 B1 | 3/2002 | Halstead et al. |
| 6,397,224 B1 | 5/2002 | Zubeldia et al. |
| 6,415,295 B1 | 7/2002 | Feinberg |
| 6,421,650 B1 | 7/2002 | Goetz |
| 6,424,996 B1 * | 7/2002 | Killcommons et al. ....... 709/206 |
| 6,564,256 B1 | 5/2003 | Tanaka |
| 6,591,242 B1 | 7/2003 | Karp |
| 6,671,714 B1 | 12/2003 | Weyer et al. |
| 6,934,698 B2 | 8/2005 | Judd |
| 6,954,802 B2 | 10/2005 | Sutherland et al. |
| 7,039,628 B2 | 5/2006 | Logan, Jr. |
| 7,118,024 B1 | 10/2006 | Hoshino |
| 7,162,571 B2 | 1/2007 | Kilian et al. |
| 7,181,017 B1 | 2/2007 | Nagel et al. |
| 7,213,022 B2 | 5/2007 | Whelan et al. |
| 7,240,150 B1 | 7/2007 | Todd et al. |
| 7,266,556 B1 | 9/2007 | Coates |
| 7,295,988 B1 | 11/2007 | Reeves |
| 7,298,836 B2 | 11/2007 | Wellons |
| 7,328,303 B1 | 2/2008 | Waterhouse et al. |
| 7,366,836 B1 | 4/2008 | Todd et al. |
| 7,379,605 B1 | 5/2008 | Ticsa |
| 7,398,391 B2 | 7/2008 | Carpentier et al. |
| 7,415,731 B2 | 8/2008 | Carpentier et al. |
| 7,418,599 B2 | 8/2008 | Peters |
| 7,428,611 B1 | 9/2008 | Todd et al. |
| 7,434,057 B2 | 10/2008 | Yagawa |
| 7,448,533 B2 * | 11/2008 | Ito .................. 235/375 |
| 7,475,432 B2 | 1/2009 | Carpentier et al. |
| 7,487,551 B2 | 2/2009 | Carpentier et al. |
| 7,519,591 B2 * | 4/2009 | Landi et al. ......................... 1/1 |
| 7,523,489 B2 | 4/2009 | Bossemeyer et al. |
| 7,530,115 B2 | 5/2009 | Carpentier et al. |
| 7,539,813 B1 | 5/2009 | Todd et al. |
| 7,546,486 B2 | 6/2009 | Slik et al. |
| 7,552,340 B2 | 6/2009 | Ooi et al. |
| 7,552,356 B1 | 6/2009 | Waterhouse et al. |
| 7,590,672 B2 | 9/2009 | Slik et al. |
| 7,591,022 B2 | 9/2009 | Carpentier et al. |
| 7,621,445 B2 | 11/2009 | Esseiva et al. |
| 7,640,271 B2 | 12/2009 | Logan, Jr. |
| 7,657,581 B2 | 2/2010 | Orenstein et al. |
| 7,694,331 B2 | 4/2010 | Vesikivi et al. |
| 7,734,603 B1 | 6/2010 | McManis et al. |
| 7,797,546 B2 | 9/2010 | Kenson |
| 7,836,493 B2 | 11/2010 | Xia et al. |
| 7,974,924 B2 * | 7/2011 | Holla et al. ..................... 705/51 |
| 8,045,214 B2 | 10/2011 | Samari |
| 8,059,304 B2 | 11/2011 | Samari |
| 2001/0027402 A1 | 10/2001 | Ramsaroop |
| 2002/0010679 A1 | 1/2002 | Felsher |
| 2002/0083030 A1 | 6/2002 | Yang et al. |
| 2002/0085476 A1 | 7/2002 | Samari-Kermani |
| 2002/0103675 A1 | 8/2002 | Vanelli |
| 2002/0103811 A1 | 8/2002 | Frankhauser et al. |
| 2002/0120470 A1 | 8/2002 | Trice, Sr. |
| 2002/0138524 A1 | 9/2002 | Ingle et al. |
| 2003/0005464 A1 | 1/2003 | Gropper et al. |
| 2003/0040940 A1 | 2/2003 | Nehammer |
| 2003/0167395 A1 | 9/2003 | Chang et al. |
| 2003/0182564 A1 | 9/2003 | Lai et al. |
| 2003/0220822 A1 | 11/2003 | Fiala et al. |
| 2004/0006492 A1 | 1/2004 | Watanabe |
| 2004/0078236 A1 | 4/2004 | Stoodley et al. |
| 2004/0083123 A1 | 4/2004 | Kim et al. |
| 2004/0172538 A1 | 9/2004 | Satoh et al. |
| 2004/0186746 A1 | 9/2004 | Angst et al. |
| 2004/0187012 A1 | 9/2004 | Kohiyama et al. |
| 2004/0187027 A1 | 9/2004 | Chan |
| 2004/0199762 A1 | 10/2004 | Carlson et al. |
| 2004/0210458 A1 | 10/2004 | Evans et al. |
| 2005/0055560 A1 | 3/2005 | Kendon |
| 2005/0075909 A1 | 4/2005 | Flagstad |
| 2005/0086082 A1 | 4/2005 | Braunstein et al. |
| 2005/0125252 A1 | 6/2005 | Schoenberg et al. |
| 2005/0125254 A1 | 6/2005 | Schoenberg |

(56) References Cited

U.S. PATENT DOCUMENTS

| | | |
|---|---|---|
| 2005/0125258 A1 | 6/2005 | Yellin et al. |
| 2005/0144172 A1 | 6/2005 | Kilian et al. |
| 2005/0192837 A1 | 9/2005 | Fears et al. |
| 2005/0197859 A1 | 9/2005 | Wilson et al. |
| 2005/0216313 A1 | 9/2005 | Claud et al. |
| 2005/0267863 A1 | 12/2005 | Carpentier et al. |
| 2006/0080307 A1 | 4/2006 | Carpentier et al. |
| 2006/0085226 A1 | 4/2006 | Kamber |
| 2006/0085347 A1 | 4/2006 | Yiachos |
| 2006/0107032 A1 | 5/2006 | Paaske et al. |
| 2006/0109518 A1 | 5/2006 | Martin et al. |
| 2006/0118614 A1 | 6/2006 | Rose |
| 2006/0155584 A1 | 7/2006 | Aggarwal |
| 2006/0179112 A1 | 8/2006 | Weyer et al. |
| 2006/0206361 A1 | 9/2006 | Logan, Jr. |
| 2006/0242144 A1 | 10/2006 | Esham et al. |
| 2006/0251073 A1 | 11/2006 | Lepel et al. |
| 2007/0014455 A1 | 1/2007 | Howerton, Jr. |
| 2007/0027715 A1 | 2/2007 | Gropper |
| 2007/0050212 A1 | 3/2007 | Kearby et al. |
| 2007/0061170 A1 | 3/2007 | Lorsch |
| 2007/0101133 A1 | 5/2007 | Liu et al. |
| 2007/0180509 A1 | 8/2007 | Swartz et al. |
| 2007/0192140 A1 | 8/2007 | Gropper |
| 2007/0234073 A1 | 10/2007 | Cromer et al. |
| 2007/0258638 A1 | 11/2007 | Howerton, Jr. |
| 2008/0005030 A1 | 1/2008 | Schlarb et al. |
| 2008/0013365 A1 | 1/2008 | Yueh |
| 2008/0065718 A1 | 3/2008 | Todd et al. |
| 2008/0071577 A1 | 3/2008 | Highley |
| 2008/0183504 A1 | 7/2008 | Highley |
| 2008/0183719 A1 | 7/2008 | Kageyama et al. |
| 2008/0208919 A1 | 8/2008 | I Dalfo et al. |
| 2008/0222042 A1 | 9/2008 | Moore et al. |
| 2008/0222654 A1 | 9/2008 | Xu et al. |
| 2008/0235759 A1 | 9/2008 | McCarty |
| 2008/0244196 A1 | 10/2008 | Shitomi et al. |
| 2008/0250506 A1 | 10/2008 | Rabischong et al. |
| 2008/0285759 A1 | 11/2008 | Shaw |
| 2008/0306872 A1 | 12/2008 | Felsher |
| 2008/0313236 A1 | 12/2008 | Vijayakumar et al. |
| 2008/0319798 A1 | 12/2008 | Kelley |
| 2009/0012813 A1 | 1/2009 | Berzansky et al. |
| 2009/0043828 A1 | 2/2009 | Shitomi |
| 2009/0055924 A1 | 2/2009 | Trotter |
| 2009/0089335 A1 | 4/2009 | Shitomi et al. |
| 2009/0119764 A1 | 5/2009 | Applewhite et al. |
| 2009/0132775 A1 | 5/2009 | Otani et al. |
| 2009/0157987 A1 | 6/2009 | Barley |
| 2009/0198515 A1 | 8/2009 | Sawhney |
| 2009/0204433 A1 | 8/2009 | Darian et al. |
| 2009/0219411 A1 | 9/2009 | Marman et al. |
| 2009/0240764 A1 | 9/2009 | Peleg et al. |
| 2009/0252480 A1 | 10/2009 | Wright |
| 2009/0319736 A1 | 12/2009 | Otani et al. |
| 2010/0138446 A1 | 6/2010 | Canessa et al. |
| 2010/0174750 A1 | 7/2010 | Donovan et al. |
| 2010/0286997 A1 | 11/2010 | Srinivasan |

FOREIGN PATENT DOCUMENTS

| | | |
|---|---|---|
| EP | 0781032 | 6/1997 |
| EP | 0952726 | 10/1999 |
| GB | 2096440 | 10/1982 |
| GB | 2380345 | 9/2001 |
| WO | WO 02/07040 | 1/2002 |
| WO | WO 2007/138603 | 12/2007 |
| WO | WO 2008/058055 | 5/2008 |
| WO | WO 2008/084330 | 7/2008 |

OTHER PUBLICATIONS

The Written Opinion, PCT/US2009/054799, dated Mar. 3, 2011.
Security of Patient and Study Data Associated with DICOM Images when Transferred Using Compact Disc Media, Fintan J. McEvoy et al., Journal of Digital Imaging; The Journal of the Society for Computer Applications in Radiology, Aug. 2007.
Handbook of Applied Cryptography, Key Management Techniques, Menezes et al., Handbook of Applied Cryptography, Jan. 1996.
European Response to the Communication Pursuant to Rule 161(1) and 162 EPC, dated May 13, 2011.
Ferelli, Mark, Content-addressable storage—Storage as I See it, Computer Technology Review, http://findarticles.com/p/articles/mi_m0BRZ/is_10_22/ai_98977101/, Oct. 2002, in 2 pages.
HoneyComb Fixed Content Storage, Solaris, http://hub.opensolaris.org/bin/view/Project+honeycomb/Webhome, Oct. 26, 2009 in 2 pages.
International Search Report and Written Opinion issued in PCT/US2009/061890, dated Dec. 10, 2009.
International Search Report and Written Opinion issued in PCT/US2011/033647, dated Nov. 28, 2011.
International Search Report and Written Opinion issued in PCT/US2011/063987, dated Sep. 6, 2012.
Mellor, Chris, Making a Hash of File Content, Techworld, http://features.techworld.com/storage/235/making-a-hash-of-file-content/?, Dec. 3, 2009, in 2 pages.
Quinlan, S., et al., Venti: a new approach to archival storage, doc.cat-v.org/plan_9/4th_edition/papers/venti, in 20 pages.
Rhea, S., et al., Fast, Inexpensive Content-Addressed Storage in Foundation, http://doc.cat-v.org/plan_9/misc/foundation/, in 22 pages.
Tolia, N., et al., Opportunistic Use of Content Addressable Storage for Distributed File Systems, USENIX Association, Jun. 9, 2003, in 15 pages.
Twisted Storage, http://twistedstorage.sourceforge.net/index.html, in 7 pages.
Twisted Storage, http://twistedstorage.sourceforge.net/news.html, in 1 page.
Medical Imaging Magazine, Jan. 2000. Product Showcase, Automated Dicom Exchange Station. 1 page.
Terry May Titled "Medical Information Security: the Evolving Challeneege" copyright 1998 IEEE doc #0-7803-4535-5/98 pp. 85-92.
Ted Cooper Titled "Kaiser Permanente Anticipates High Cost as it Gears up for HIPAA" IT Health Care Strategist vol. 1, No. 10 Oct. 1999 p. 4.
Haufe G. et al.: PACS at Work: A Multimedia E-Mail Tool for the Integration of Voices and Dynamic Annotation, Computer Assisted Radiology, Proceedings of the International Symposium, 1998 Etsevier Science B.V., pp. 417-420.
Dimitroff D C et al: "An Object Oriented Approach to Automating Patient Medical Records" Proceedings of the International Computer Software and Applications Conference. (Compsac), US, Washington, IEEE. Comp. Soc. Press, vol. CONF. 14, 1990, pp. 82-87.
Kleinholz L et al: "Multimedia and PACS. Setting the Platform for Improved and New Medical Services in Hospitals and Regions" Car '96 Computer Assisted Radiology. Proceedings of the International Symposium on Computer and Communication Systems for Image Guided Diagnosis and Therapy, Paris, France, Jun. 1996, pp. 313-322, XP002083080 1996, Amsterdam, Netherlands, Elsevier, Netherlands, ISBN: 0-444-82497-9.
1996 Annual HIMSS Conference and Exhibition, Managing Care: The Race Is On, dated Mar. 3-7, 1996.
FilmX Presentation Slides.
Candelis website excerpt, http://www.candelis.com via the Internet Wayback Machine (Archive.org), Jul. 19, 2010.
Carestream website excerpt, http://carestreamhealth.com via the Internet Wayback Machine (Archive.org), Nov. 20, 2010.
eMix website excerpt, http://www.emix.com via the Internet Wayback Machine (Archive.org), Jul. 10, 2011.
GE Healthcare IT website excerpt, http://www.dynamic-imaging.com via the Internet Wayback Machine (Archive.org), Jan. 27, 2010.
HeartIT website excerpt, http://heartit.com via the Internet Wayback Machine (Archive.org), Jan. 29, 2009.
Infinitt North America website excerpt, http://infinittna.com via the Internet Wayback Machine (Archive.org), Feb. 28, 2009.

(56) References Cited

OTHER PUBLICATIONS

InSite One website excerpt, http://www.insiteone.com via the Internet Wayback Machine (Archive.org), Aug. 8, 2010.
LifeIMAGE website excerpt, http://www.lifeimage.com via the Internet Wayback Machine (Archive.org), Nov. 4, 2010.
McKesson website excerpt, http://www.mckesson.com via the Internet Wayback Machine (Archive.org), Oct. 20, 2010.
MyMedicalRecords.com website excerpt, http://www.mymedicalrecords.com via the Internet Wayback Machine (Archive.org), Aug. 1, 2010.
PACS Image website excerpt, http://www.pacsimage.com via the Internet Wayback Machine (Archive.org), Apr. 2, 2010.
ScImage website excerpt, http://www.scimage.com via the Internet Wayback Machine (Archive.org), Sep. 27, 2010.
See My Radiology website excerpt, http://www.seemyradiology.com via the Internet Wayback Machine (Archive.org), Jul. 11, 2010.
Symantec Health Press Release, http://www.symantec.com/about/news/release/article.jsp?prid=20100819_01, Aug. 19, 2010.
XRAYLINE website excerpt, http://www.xrayline.com via the Internet Wayback Machine (Archive.org), Oct. 13, 2010.

* cited by examiner

SYSTEM AND METHOD OF ENCRYPTION FOR DICOM VOLUMES

CROSS-REFERENCE TO RELATED APPLICATIONS

This application claims priority to U.S. Provisional Patent Application No. 61/091,161, filed on Aug. 22, 2008, and to U.S. Provisional Patent Application No. 61/119,012, filed on Dec. 1, 2008, the entire contents of each of which are hereby incorporated by this express reference.

BACKGROUND

1. Field

This disclosure relates to the Digital Imaging and Communications in Medicine (DICOM) standard for handling, storing, printing, transmitting, and distributing medical imaging information and, more specifically, to encrypting DICOM volumes and accessing encrypted DICOM volumes.

2. Description of the Related Art

Picture archiving and communication systems (PACS) are computers or networks dedicated to the storage, retrieval, distribution, and presentation of medical data. For example, PACS are frequently used to store medical image data in the Digital Imaging and Communications in Medicine (DICOM) format, which is a standard for handling, storing, printing, and transmitting medical images. DICOM provides a standardized file format and network communications protocol. The communication protocol is an application protocol that uses TCP/IP to communicate between systems. DICOM is prevalent because it enables the integration of modalities, such as scanners, servers, workstations, printers, and network hardware from multiple manufacturers into a PACS.

Certain PACS comprise systems for recording medical data such as medical images onto removable media. These portable digital recording media offer a number of advantages to users, such as allowing users to access their medical data from home, conveniently transporting medical data to a new physician or to a specialist, and the like. However, these media are vulnerable to theft, loss, copying, etc. Part Ten (10) ("Part 10") of the DICOM standard has attempted to define systems for creating secure (e.g., encrypted) volumes for storing medical data. Part 10 of the Standard advantageously permits a user via a Graphical User Interface (GUI) to select one or more patients, studies, series, or images for which associated images will be written and/or labeled into one or more encrypted volumes using different types of applicable media (e.g., Blu-ray, CD, DVD, memory stick, USB flash drive, etc.). However, a significant problem remains in that a person desiring to access the stored medical data may not remember or know the key (e.g., password) for "unlocking" encrypted medical data.

Accordingly, there is a need for an encrypted digital DICOM data management system which reduces access time and which requires less intervention by medical facility personnel.

SUMMARY

Because of confidentiality mechanisms and procedures, access to DICOM volumes holding confidential patient information (e.g., medical data) is typically restricted within a medical facility's computer network. After the DICOM volumes leave the medical facility, however, the volumes become susceptible to access by unauthorized users. Various embodiments provide methods and systems to encrypt and provide access to encrypted medical data stored on a portable digital recording medium, such that only authorized users can read the contents of the medium. By providing an encryption and decryption methods and systems for the volumes and by allowing authorized access to decryption (i.e., access) passwords, patient confidentiality can be maintained. The systems and methods disclosed herein can permit authorized users to access encrypted data stored on the portable medium even if the users do not have access to the original encryption mechanism. Thus, encrypted data stored on the volume can be easily and securely accessed by a variety of authorized users.

In at least one embodiment, a computer-implemented system for providing access to securely stored medical data is provided. The system can include a database configured to store decryption passwords for decrypting encrypted medical data stored on a portable medium; a secure interface configured to authenticate a request for decryption of medical data stored on the portable medium; and a password retrieval service. The password retrieval service can be configured to receive the authenticated request from the secure interface; and to retrieve from the database a decryption password uniquely associated with medical data stored on the portable medium, wherein the portable medium is associated with one decryption password. The password retrieval service can be further configured to communicate the decryption password for accessing medical data stored on the portable medium, wherein the decryption password is used for transforming the encrypted medical data into plaintext.

In at least one embodiment, a computer-implemented method of providing access to an encrypted medical data stored on a portable medium is provided. The method can include the steps of authenticating a user; retrieving a decryption key associated with the portable medium; accessing a security mechanism stored on the portable medium and retrieving a decryption password; and comparing the decryption key with the decryption password. When there is a match, the method can include transforming the encrypted medical data stored on the portable medium into format accessible by the user, wherein the decryption key is used for transforming the encrypted medical data into plaintext.

In at least one embodiment, a computer-implemented method of creating portable medium comprising encrypted medical data is provided. The method can include the steps of receiving medical data from one or more modalities; selecting a subset of the received medical data to be included on a portable medium; encrypting the subset of medical data using an encryption mechanism; generating a security mechanism for decrypting the encrypted medical data, wherein the security mechanism is used for transforming the encrypted medical data into plaintext; and recording the encrypted medical data on a portable medium.

In certain embodiments, the security mechanism stored on the portable medium can be encrypted.

In certain embodiments, the security mechanism can be selected from the group consisting of CMS, PKCS #5, SHA-1, MD5, RSA, AES, and DES.

In at least one embodiment, a computer-implemented method of creating portable medium comprising encrypted medical data is disclosed. The method can include the steps of receiving medical data from one or more modalities; selecting a subset of the received medical data to be included on a portable medium; encrypting the subset of medical data using an encryption mechanism; determining a security mechanism for decrypting the encrypted medical data, wherein the security mechanism uniquely corresponds to a user of the portable medium such that the user is associated with one security mechanism; and recording the encrypted medical data on a portable medium.

In certain embodiments, the security mechanism can be recorded on the portable medium.

In certain embodiments, the security mechanism can be a password used for transforming the encrypted medical data into plaintext.

In certain embodiments, the encryption mechanism can be selected from the group consisting of CMS, PKCS #5, SHA-1, MD5, RSA, AES, and DES.

In at least one embodiment, a computer-implemented system for providing access to securely stored medical data is disclosed. The system can include a database configured to store a decryption password for decrypting medical data stored on a portable medium, wherein the decryption password is generated from information comprised in at least one tag associated with medical data. The system can further include a secure interface configured to authenticate a request for decryption of medical data stored on the portable medium and a password retrieval services. The password retrieval service can be configured to receive the authenticated request from the secure interface; receive information comprised in the at least one tag; retrieve from the database the decryption password uniquely associated with medical data stored on the portable medium, wherein one decryption password is associated with information comprised in the at least one tag; and communicate the decryption password for accessing medical data stored on the portable medium, wherein the decryption password is used for transforming the encrypted medical data into plaintext.

In certain embodiments, the at least one tag can be a DICOM tag.

In certain embodiments, the secure interface can be a secure web interface.

In certain embodiments, medical data can be represented in DICOM format.

These and other features and advantages of the invention will become apparent from the following description of embodiments. Neither this summary nor the following detailed description purports to define the invention. The invention is defined only by the claims.

BRIEF DESCRIPTION OF THE DRAWINGS

These and other features will now be described with reference to the drawing summarized below. These drawings and the associated description are provided to illustrate specific embodiments, and not to limit the scope of the invention.

DETAILED DESCRIPTION

In the following detailed description, references are made to the accompanying drawings that illustrate specific embodiments in which the invention may be practiced. Electrical, mechanical, programmatic and structural changes may be made to the embodiments without departing from the spirit and scope of the disclosure. The following detailed description is, therefore, not to be taken in a limiting sense and the scope of the disclosure is defined by the appended claims and their equivalents.

Figure 1:
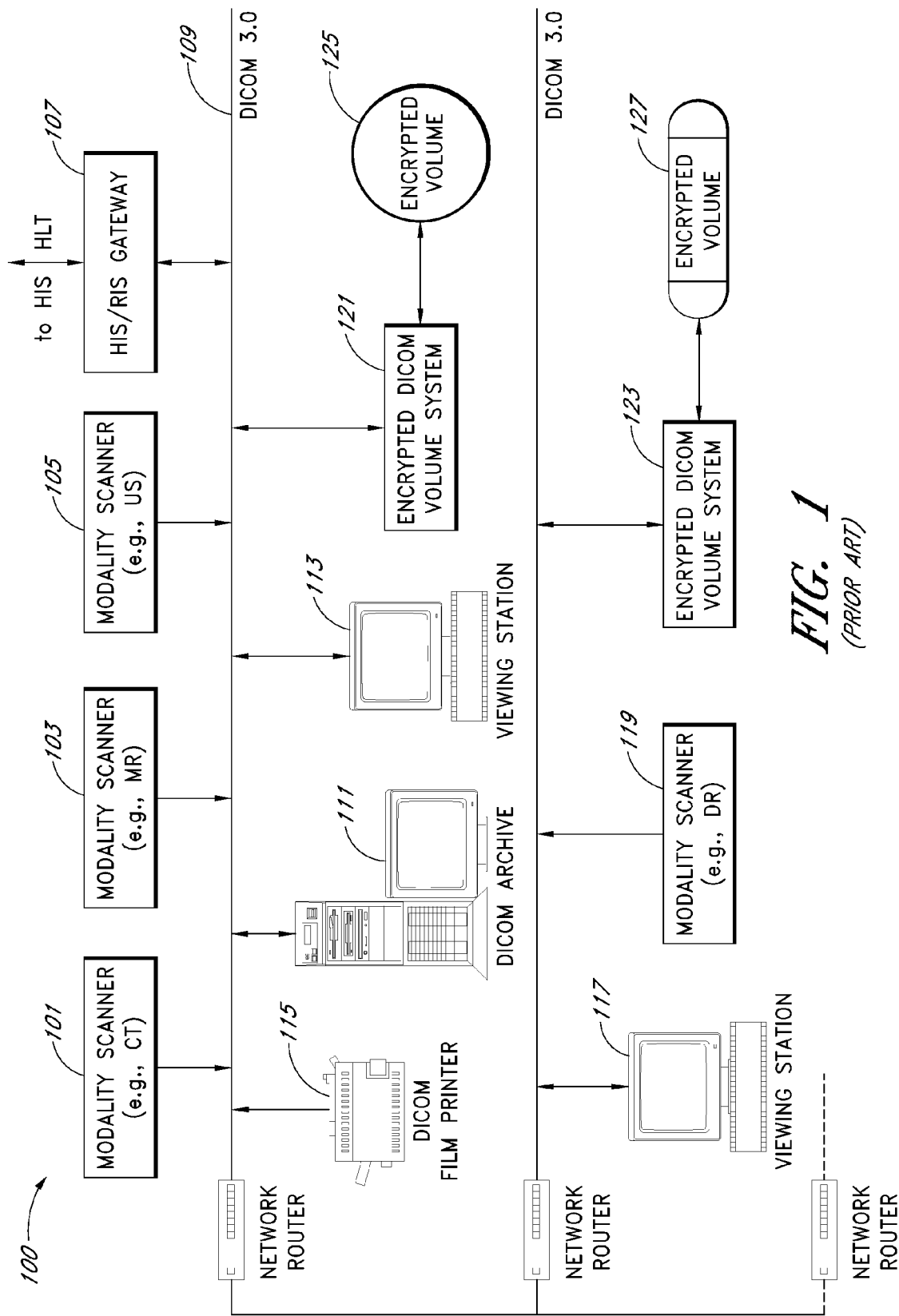
FIG. 1 illustrates a block diagram of a Picture Archiving and Communications System (PACS).

FIG. 1 illustrates a block diagram of a PACS digital image management system 100. The system can include a plurality of input imaging devices, a plurality of output imaging devices, a plurality of image display stations and archive server communicatively interconnected via a network. Each input imaging device can be an image-generating device capable of producing a digital image. For example, in a medical imaging environment input imaging devices can be a variety of medical imaging modalities such as computed tomography (CT) 101, digital radiography (DR) 119, magnetic resonance (MR) 103, and/or ultrasound (US) devices 105, manufactured by a number of different manufacturers, such as General Electric, Phillips, Siemens, Toshiba, and others.

The digital images produced by input imaging devices can be communicated via a network to output imaging devices (e.g., viewing stations 113 and 117, film printer 115, etc.), display stations, and an archive. In addition to communicating the generated images, the input imaging device can communicate customer specific information. For example, in a medical environment input-imaging devices can communicate a patient's name, a physician's name and a modality type. In at least one embodiment, images are communicated over network using a data communications protocol developed by the American College of Radiology (ACR) and the National Electrical Manufacturers Association (NEMA) known as the DICOM protocol (e.g., DICOM 3.0).

The DICOM protocol can be implemented using a TCP/IP connection 109 between the communicating devices Health information systems (HIS) and radiology information systems (RIS) gateway 107 providing medical data, such as in the HL-7 format, can be connected via connection 109.

The archive 111 can store digital images and reports received from the modalities over the network according to the customer specific information associated with the image. The archive can initially store the received object on "short-term" storage device (e.g., NAS, RAID). The archive can manage a database (not shown) in order to maintain information about each image, including the location of each image. The database can be centralized or distributed.

Upon request by a user, such as a radiologist or radiology technician, or by another device (e.g., HIS-RIS broker), the archive 111 can retrieve stored objects from a managed storage device and communicates the images and reports to display stations 113 and 117 for viewing. In addition, the archive 111 can communicate the retrieved images to output imaging devices to produce a hardcopy output of the retrieved image. In a medical environment, output imaging devices can be continuous tone laser imagers for forming an image on an imaging element.

Output imaging devices can also include a processor station (e.g., a DICOM film printer 115) for chemical processing and developing of the output image formed on a photographic element. The element can be photo-thermographic and can be thermally processed and need not be chemically processed. Other imaging processes are also suitable for output imaging devices, including direct thermal imaging, ablation imaging, dye transfer, inkjet, dye sublimation and thermal mass transfer.

In some embodiments, medical data can be communicated to encrypted DICOM volume systems 121 and 123 for storage on an encrypted volume according to the DICOM Part 10 standard. For example, the encrypted volume can be an optical disk (e.g., a CD, DVD, Blu-Ray, etc.) 125 or a removable memory (e.g., flash) device 127.

Figure 2:
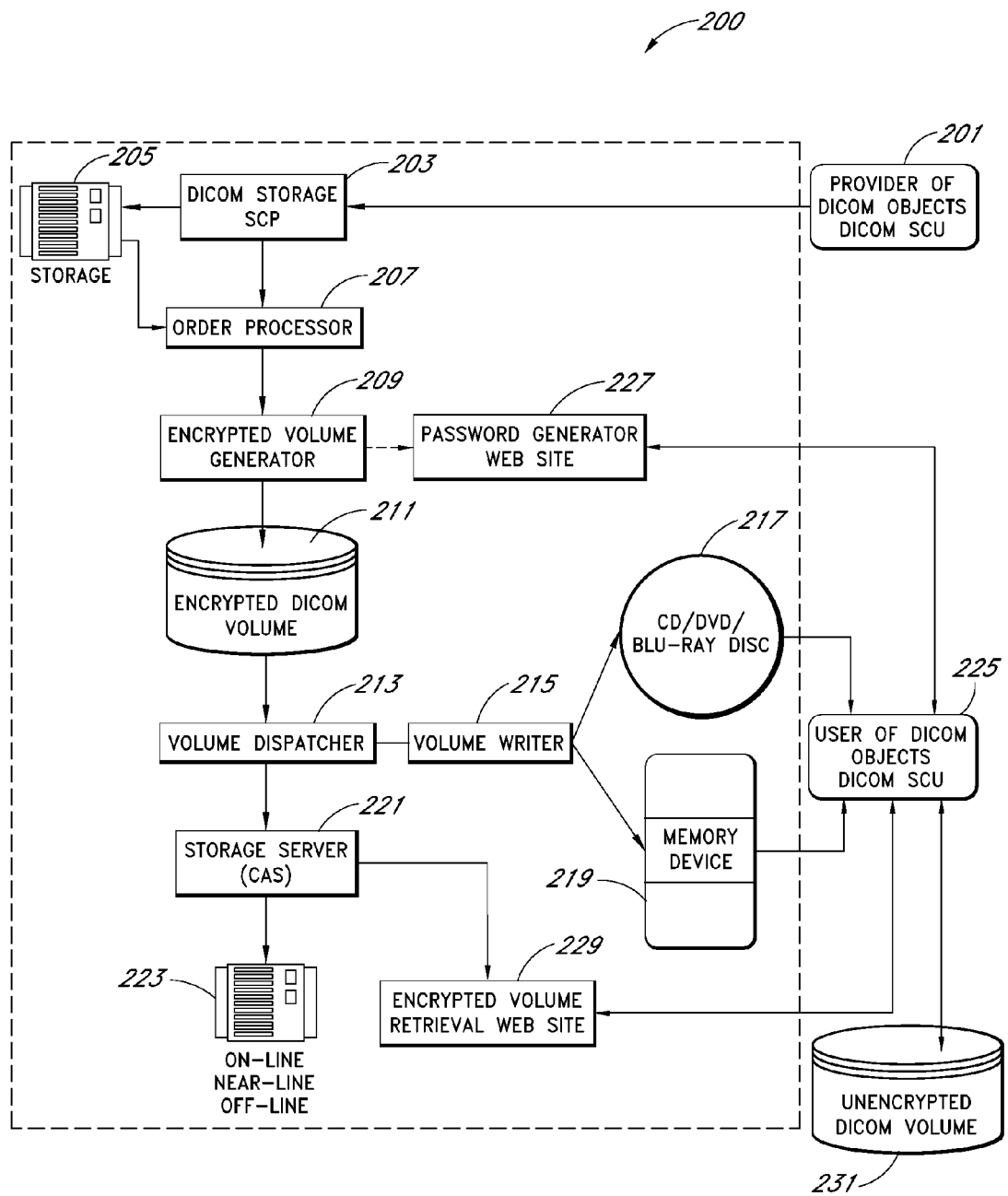
FIG. 2 illustrates a block diagram of a system for secure storage and retrieval of DICOM data.

FIG. 2 illustrates a system 200 for secure storage and retrieval of DICOM objects. In some embodiments, a provider of DICOM objects 201 can send DICOM objects for storage. DICOM objects can be stored in a disk configuration (e.g., Direct Attached Storage (DAS), Network Attached Storage (NAS) or Storage Area Network (SAN) or be sent to a Content Addressable Storage (CAS) server (e.g., iCAS server). The provider 201 can act as a DICOM storage service class user (SCU), and the DICOM storage module 203 can store the DICOM objects in storage 205 as the objects are received.

At some point in time, such as based on an automatic (set by schedules) order or manual (generated by users) order, a set of one or more DICOM objects can be selected by an order processor 207 to be included in an encrypted DICOM Part 10 volume 211. The volume 211 can comprise medical data, a DICOMDIR directory (according to the DICOM Part 10 specifications), and one or more DICOM viewers. Additional data can be included (e.g., text file with a list of DICOM objects, text file holding the customer string of the USB license dongle connected to the computer system generating the encrypted volume, etc.). The volume 211 can be generated by an encrypted volume generator 209 by writing the contents to a container holding the original data in an encrypted fashion.

In some embodiments, at least some of the files (e.g., DICOM objects, DICOMDIR, viewers, etc.) that make up a volume can be written to an optical disc or memory stick and properly labeled and stored in a storage server for later retrieval. Accordingly, the volume 211 can be stored on removable media or in a content addressable storage (CAS). A volume dispatcher 213 can dispatch the volume 211 to a volume writer 215, which stores the volume on a removable disk (e.g., a CD, DVD, Blu-ray, etc.) and/or on a removable memory (e.g., flash) device 219. The volume 211 stored on a removable disk 217 or memory device 209.

As mentioned above, the volume dispatcher 213 can store the volume 211 in a storage server 221. In some embodiments, the storage server can be a CAS server. As is known in the art, CAS implements a mechanism for storing information for later retrieval based on information's content. CAS can be used for high-speed storage and retrieval of information having fixed content. Storage server (e.g., CAS) can store the volume 211 in storage 223, which can be on-line, near line, or off-line storage.

In some embodiments, decryption (i.e., access) passwords for the encrypted volume can be generated by the password generator 227 and stored in the application (or on the removable media) used to prompt the user 225 for a valid password to access the encrypted volume. A decryption password serves as a cryptographic key and is used by a decipher algorithm or decryption algorithm (i.e., the reverse of the cipher or encryption algorithm) to decrypt data stored on the encrypted volume. Decrypted data is also known as plaintext or unencrypted data.

The user of the encrypted volume (e.g., patient, referring physician, etc.) can insert the removable disc 217 or memory device 219 in a reader. An auto run file can start a GUI application that provides the address of the password web site 227 that can be used to retrieve the passwords. The user can visit the web site specified in the label or the disc or on the memory device and enter a sequence of characters (e.g., letters, numbers, symbols, etc.) that uniquely identify the disc. The user can then be prompted to enter some information about the contents of the encrypted volume (e.g., date of birth, date of exam, etc.). In some embodiments, the information requested form the user can be part of the DICOM data (e.g., a DICOM tag) and is easy for the user to recall.

Based on the information provided by the user, the password web site 227 can return a user password that can be used to gain access to the encrypted volume 211. The user can enter the password in the field provided by the GUI on the volume. If the password is correct (i.e., matches the stored password) the utility can attempt to mount the encrypted volume 211 and execute the auto run in the container. If this operation completes, user's expectations can be similar to the one of opening a standard non-encrypted DICOM Part 10 volume. If, due to computer security policies the system is not able to mount the encrypted container, then the decrypted contents of the container can be copied to a disk drive in the computer (e.g., c:\temp\SPX).

A dialog box can be displayed indicating that the contents of the disk 217 or memory device 219 are unencrypted and are copied to the magnetic disk. In any event, encrypted data is made available in an unencrypted volume 231. The auto run in the unencrypted volume 231 can be executed in order to bring up the same interface as provided by a standard non-encrypted DICOM Part 10 volume. When the encrypted volume 211 is ejected from the computer system an attempt can be made to delete the contents of the unencrypted volume 231 from the disk drive (e.g., c:\temp\SPX).

As explained above, in some embodiments, the encrypted volume 211 can be stored in the storage server 221. Upon obtaining and entering the correct password, the user can contact an encrypted volume retrieval web site 229. The volume 211 is retrieved from the storage server 221 (by accessing storage 223) and mounted as described above.

Figure 3:
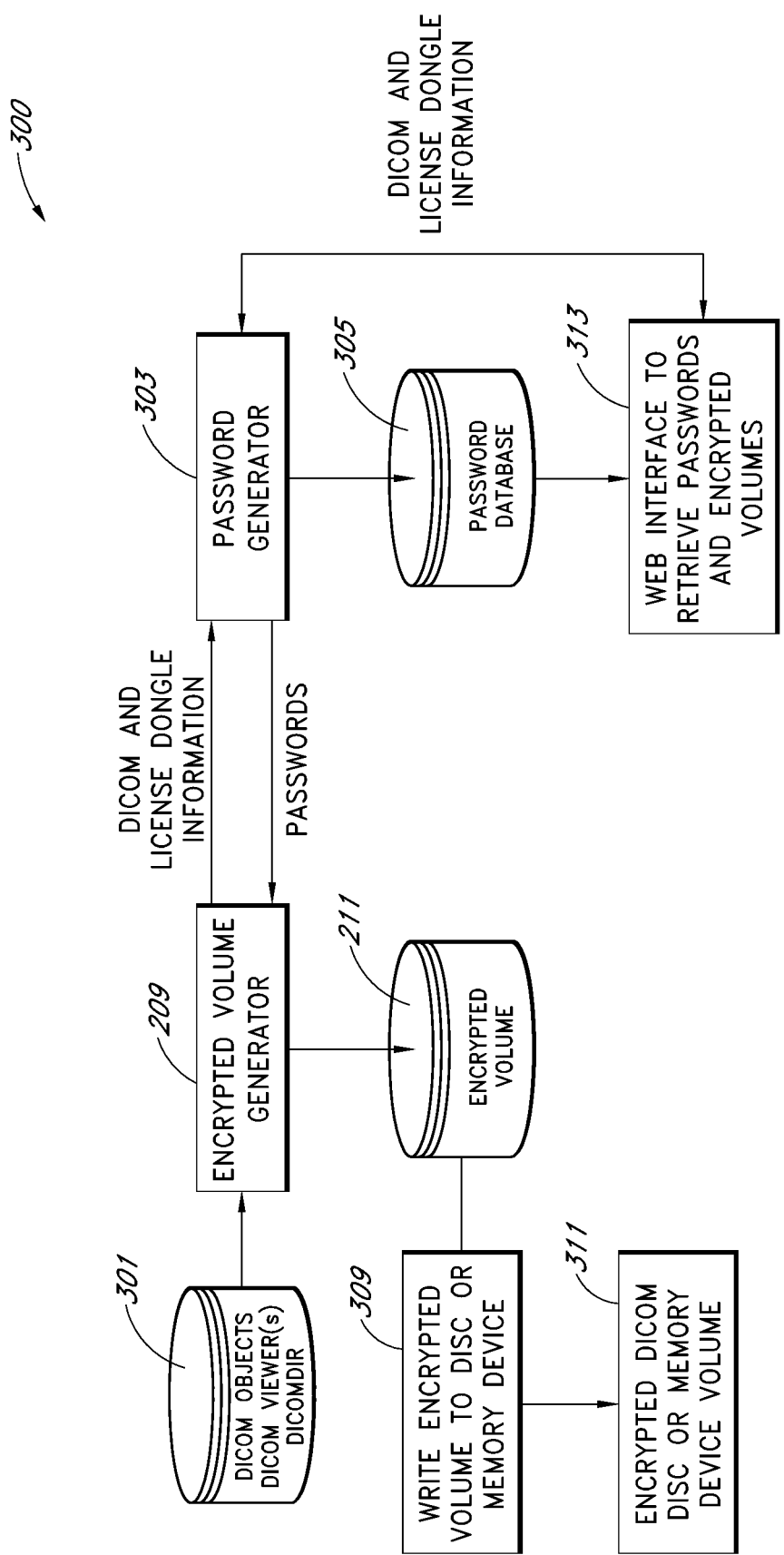
FIG. 3 illustrates a flow chart for generating passwords for encrypted DICOM Part 10 volumes in accordance with some embodiments

FIG. 3 illustrates a flow chart for generating passwords for encrypted volumes in accordance with some embodiments. Encrypted volume generator 209 can encrypt the objects (and, optionally, DICOMDIR and viewer) 301 that will be placed in a DICOM Part 10 volume 211. Password generator 303 can generate a set of passwords for the volume 211. In some embodiments, password generator 303 can generate the following passwords using as base information DICOM tags and information from the license dongle of the system generating the encrypted volume:

| Password Type | Count | Description |
| --- | --- | --- |
| USER | 1 per patient | Password generated using information from the license dongle and from the contents of one or more DICOM tags. Can be obtained from the web retrieval service. |
| FACILITY | 1 per facility | Password generated using information from the license dongle. Can be obtained from a specialized web/utility retrieval service available to each facility generating encrypted volumes. |
| SENSOR | 1 | Password generated using information from the license dongle. Can only be obtained by authorized personnel from facilities generating encrypted volumes by contacting the provider. |

Optional database 305, can store unique passwords to discs generated by a facility. Such passwords could, for example, be retrieved from the database by a web retrieval service 313 in order to allow access to encrypted volumes.

In some embodiments, a user can, at 309, write the encrypted volume 211 to a portable disc or memory device 311 and, optionally, properly label it. Further, the user can store the volume 211 permanently (e.g. to a storage server 223) to be remotely retrieved using a password. This option can eliminate the need for writing the contents of the DICOM Part 10 encrypted volume to a portable disc or memory device 311.

Figure 4:
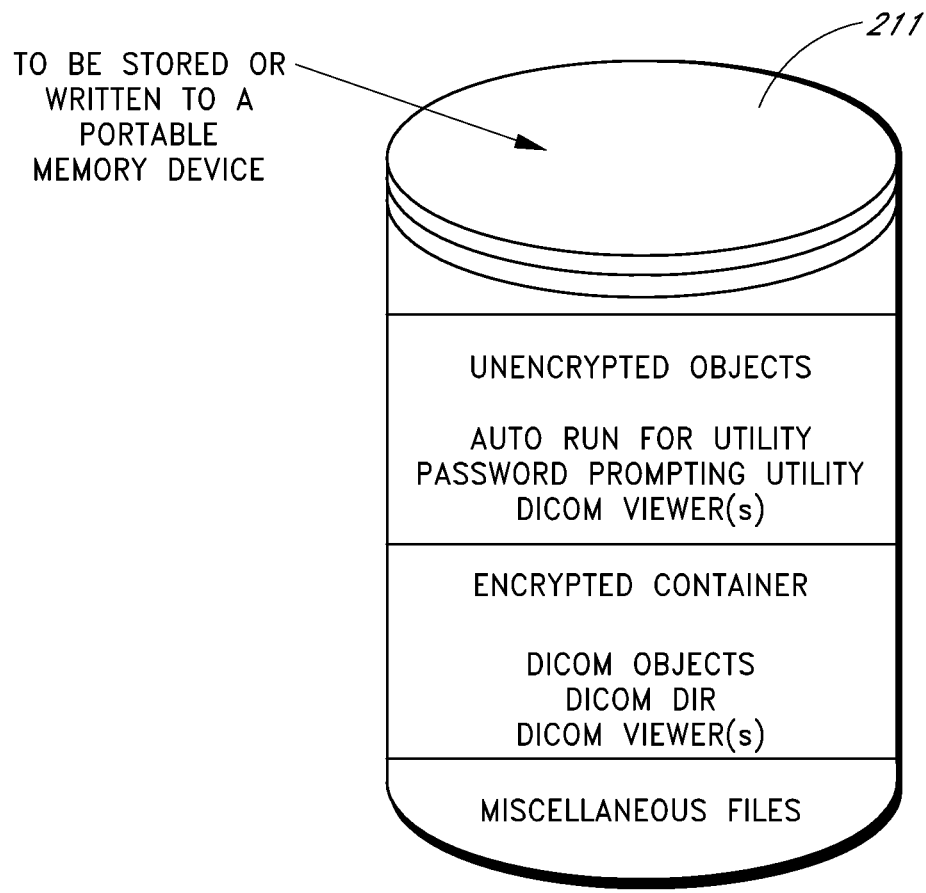
FIG. 4 illustrates a plurality of different types of encrypted DICOM Part 10 volumes (e.g., CD, DVD, Blu-ray, flash drive, etc.) implementing the encryption method in accordance with some embodiments.

FIG. 4 illustrates data that can be included in a DICOM Part 10 encrypted volume 211 according to some embodiments. The encrypted container can hold a standard non-encrypted DICOM Part 10 volume including an auto run file which would bring up the interface (e.g., DICOM viewer, HTML page, etc.) typically provided for the application. The unencrypted portion of the volume can hold files that allow auto run of a utility that:

Displays the address of a web retrieval service for obtaining a password for the encrypted volume.
Information that needs to be entered when prompted by the web retrieval service.
Prompt the user for the password provided by the web retrieval service.

The contents of the volume can:

Be written to a CD, DVD or Blu-ray disc and optionally labeled.
Be written to a portable memory device or flash type device and optionally labeled.
Stored for retrieval using a password. This can eliminate the need to write a physical encrypted volume.

Figure 5:
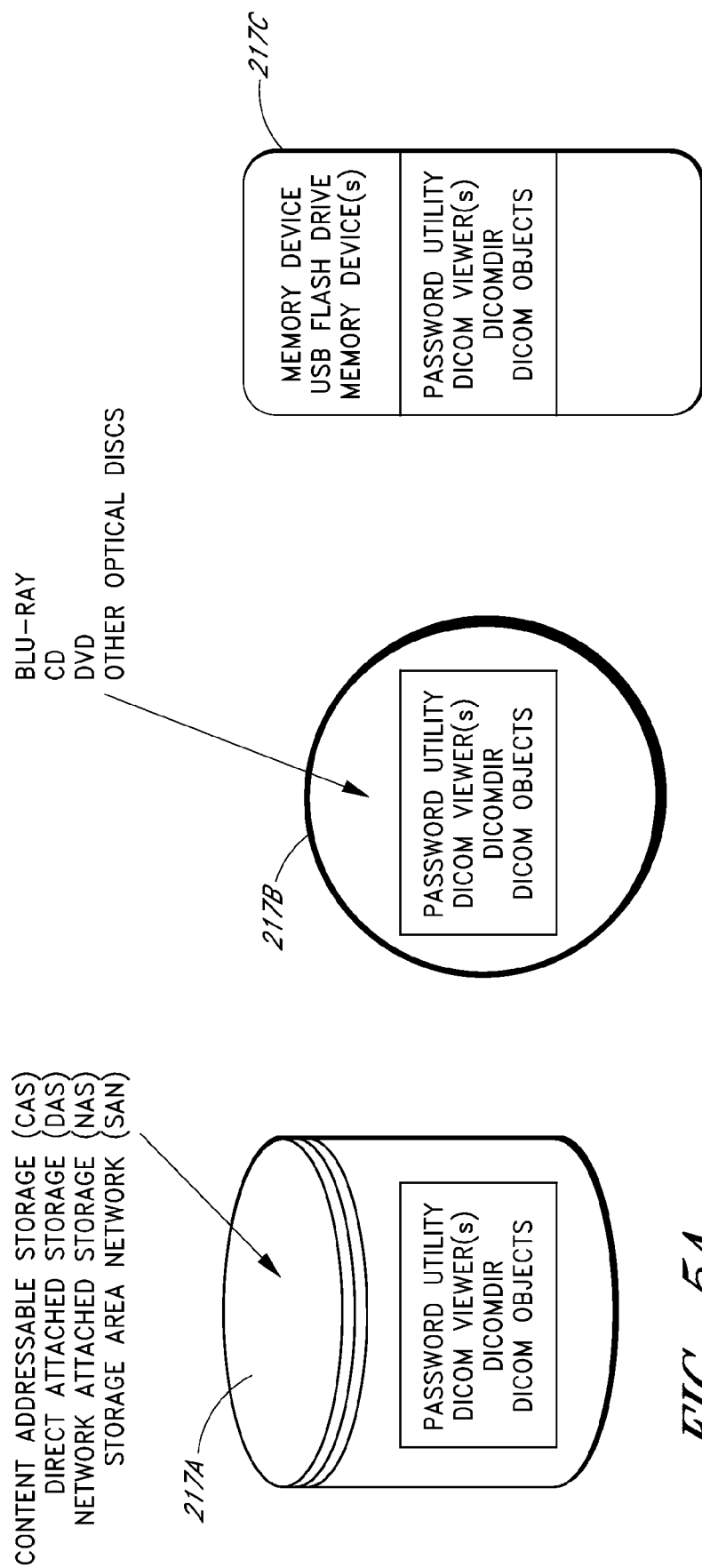
FIGS. 5A-5C illustrate encrypted DICOM Part 10 volumes and associated data stored thereon in accordance with some embodiments.

FIGS. 5A-5C illustrates a plurality of encrypted DICOM Part 10 volumes that can be generated according to some embodiments. FIG. 5A illustrates storing the contents for an encrypted volume 217A for future use. The contents can be written to any storage medium, such as an optical disc or magnetic disk drive, or can be directly downloaded via a network connection to a computer, and the like.

FIG. 5B illustrates a portable disk (e.g., Blu-ray, CD or DVD) to which the contents of the DICOM Part 10 volume 217B have been written. The other side of the volume can be used to hold an optional label for ease of volume identification. FIG. 5C illustrates a portable memory device or USB flash drive holding an encrypted DICOM Part 10 volume 217C.

In some embodiments, the volumes 217A-217C store, besides the encrypted DICOM Part 10 information, one or more DICOM viewers and/or information for accessing a password retrieval service to gain access to the encrypted components using a password. In some embodiments, the volumes 217A-217C store DICOMDIR information.

Figure 6:
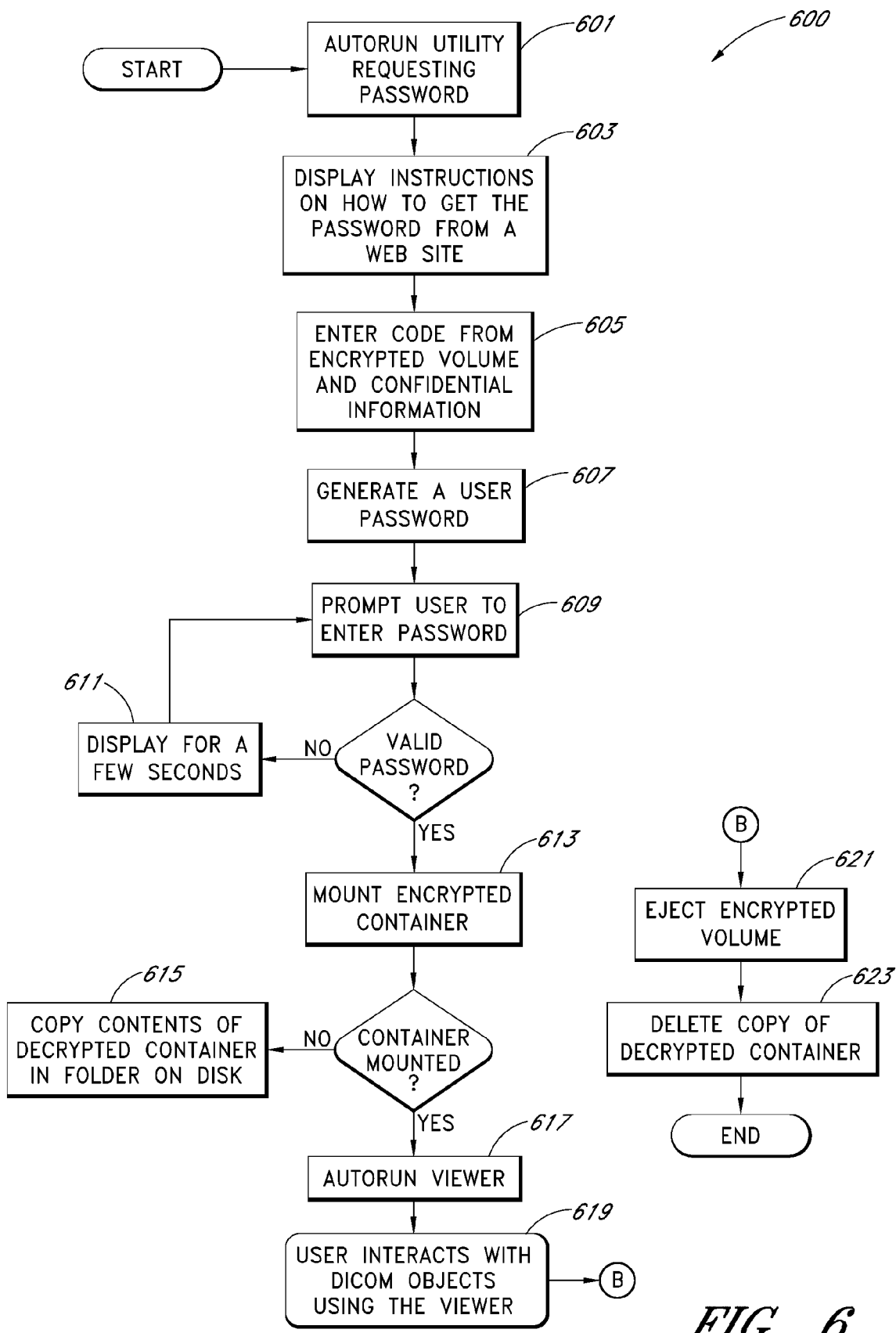
FIG. 6 illustrates a flow chart for accessing the contents of an encrypted DICOM Part 10 volume in accordance with some embodiments.

FIG. 6 is a flowchart illustrating an example method for permitting a system 600 to access an encrypted volume 211. When the encrypted volume 211 is inserted into a drive, and if the auto run facility is enabled in the computer, a utility can be started, at stage 601, and display, at 603, information on how to obtain a password from a web retrieval service. If auto run is disabled a file (e.g., \README.txt) in the volume contains information on how to manually start the utility.

The utility can display, at stage 603, information on how to connect to the web site used to retrieve user passwords. If the system 600 allows it and is connected to the Internet, a link (e.g., www.dicomdisc.com/password) can automatically take the user to the web retrieval service.

At stage 605, the web retrieval service can prompt the user for the code assigned to it when the encrypted disc was generated. The code can be found printed on the disc or in an unencrypted file (e.g., \code.txt) in the volume. In addition, the user can be required to enter some confidential information that can be part of one or more DICOM tags (e.g., date of birth, date of exam, modality of exam, etc.).

In some embodiments, the provided information can be used by the web retrieval service, at stage 607, to generate a password. In a different embodiment, a security mechanism database can be used to look up and associate the password with the information provided by the user. In any case, a password (valid or invalid) can be returned. The purpose of invalid passwords is to delay the process of trial and error to obtain a password.

The password can then be entered, at stage 609, into a utility displayed by the encrypted volume. If the password is incorrect (i.e., does not match the password generated and returned at stage 607), after a delay in stage 611 the user can be informed of the failed attempt. The user can be prompted to enter a new password. In one embodiment, if too many failed attempts have been detected, the application may exit or no longer permit further attempts. This may be done to slow down the process of obtaining a valid password by trial and error.

After a valid password is entered the encrypted container can be mounted, at stage 613, as an unencrypted volume. In some computer systems for security reasons the mount volume operation can be disabled. In such cases the utility in the encrypted volume can copy, at stage 615, the contents of the encrypted volume 211 to a folder (e.g., c:\temp\SPX) in a disk attached to the computer system. The user can then be informed that the contents of the decrypted volume are now unencrypted in a folder in the computer. The user may wish to delete the contents of the folder when done accessing the DICOM data.

After the user gains access to the encrypted container or to a copy of the decrypted data the software can attempt, at stage 617, to auto run the standard application (e.g., an image viewer) pointed to by the auto run (e.g., \autorun.ini) file. At stage 619 the user can access the DICOM data.

After the user is done accessing the decrypted data and the encrypted volume is ejected at stage 621, direct access to the data can be terminated. An attempt can also made, at stage 623, to automatically delete the contents of decrypted data if written to a folder in a disk attached to the computer system (e.g., c:\temp\SPX).

Figure 7:
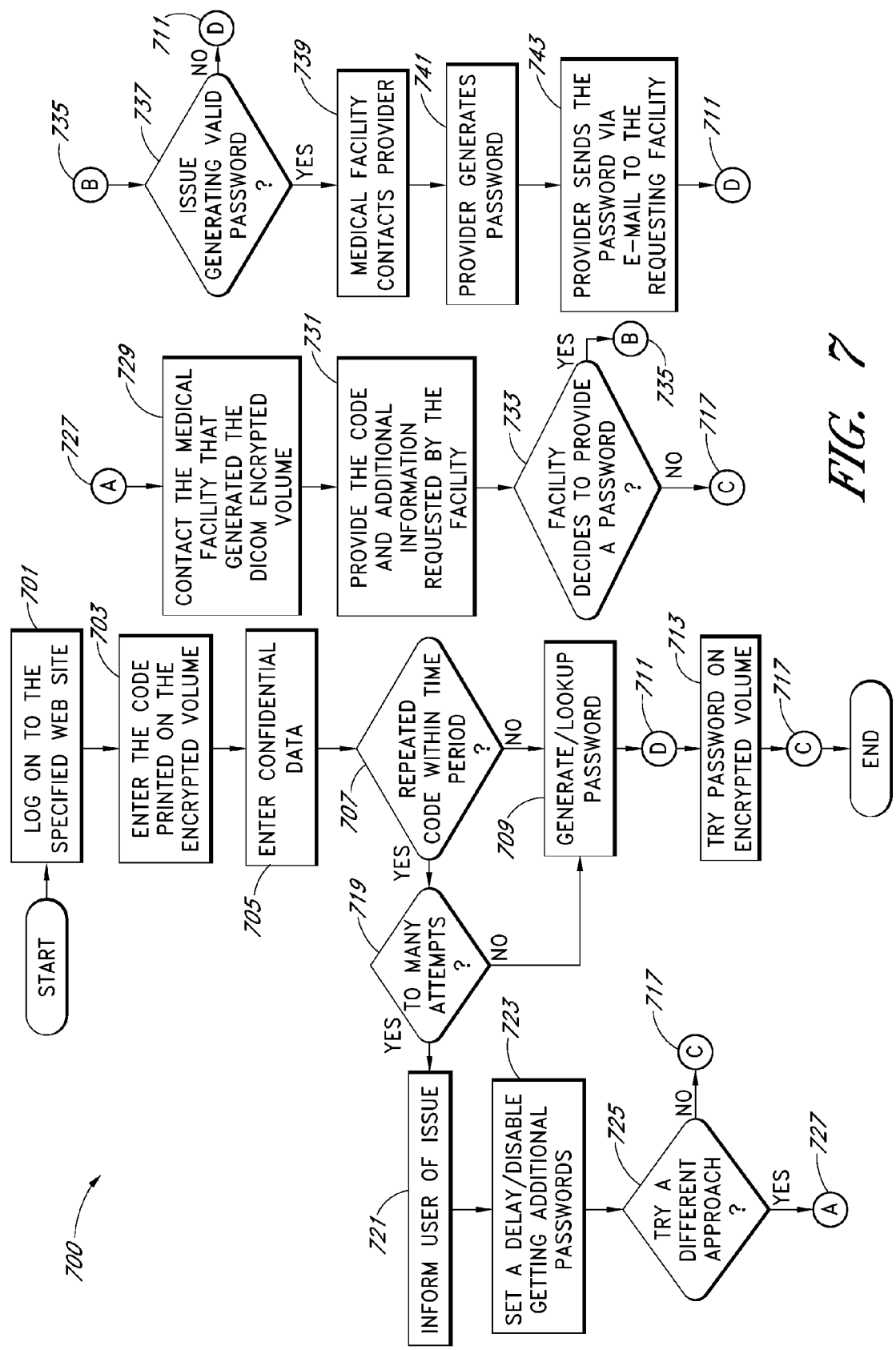
FIG. 7 illustrates a flow chart for obtaining a password to access the contents of an encrypted DICOM Part 10 volume in accordance with some embodiments.

FIG. 7 illustrates some steps taken by a system 700 for obtaining a password to access the contents of an encrypted DICOM Part 10 volume 211 in accordance with some embodiments. At stage 701, the user can be directed to access a web retrieval service (e.g., www.dicomdisc.com/password) using a standard web viewer (e.g., Internet Explorer from Microsoft). If the autorun utility senses that the machine is connected to the Internet it can attempt to connect automatically.

At stage 703, the user can be required to enter the code printed on the label of the Blu-ray, CD, DVD disc, portable memory device, or the code in a file (e.g., \code.txt located at the root directory of the encrypted volume 211). The web retrieval service can, at stage 705, prompt for confidential information known and easily recalled by the user (e.g., date of birth, type of exam, etc.).

At stage 709, the web retrieval service can check if it is able to generate the requested password. If it is able to do so, it can generate a password or, in some embodiments, look up the password in a security mechanism database. At stage 711, the password can then be presented on the screen or sent to the user via e-mail. As explained above, at stage 713 the user can enter the password in order to gain access to encrypted data. At stage 717, user's access to the data is terminated.

If the password is not valid, the procedure can be repeated a few times at stage 707. After a number of failed attempts the user, at stages 719, 721, and 723, may not be able to request a password. At stage 725, the user can be asked to try a different approach to obtain a valid password or the system 700 can decide not to try and terminate user's access at stage 717. If a different approach is decided on by the system 700, at stages 727 and 729 the user can be required to contact the facility that generated the encrypted volume. The contact information for the facility can be printed on the label of the Blu-ray, CD or DVD disc and or in a file (e.g., \contact_facility.txt) located in the root directory in the disc or memory device.

The facility that generated the encrypted disc volume can, at stage 731, request information from the user. In some embodiments, it is up to the facility to decide if they would issue a password. If the facility decides to generate or look up a password at stages 733 and 735, the medical facility can access a dedicated web site (e.g., www.datcard.com/password) or utility. At stage 737, the password generated by the medical facility may not work if the information provided is incorrect. Accordingly, at stage 739, the medical facility can contact the manufacturer of the software (e.g., DatCard Systems) and request a password using the code printed on the disc label and in a file at the root directory of the encrypted volume (e.g., \code.txt). As is explained above, at stage 741, the provider can generate the password.

To avoid authentication issues, the password can be sent, at stage 743, to a set of predefined e-mail addresses (e.g., filmroom@medicalfacility.org) associated with each specific medical facility. It can be up to the facility to provide the password to the user. At stage 733, the medical facility can decide not to provide the password to the user and the session can be terminated at stage 717.

Figure 8:
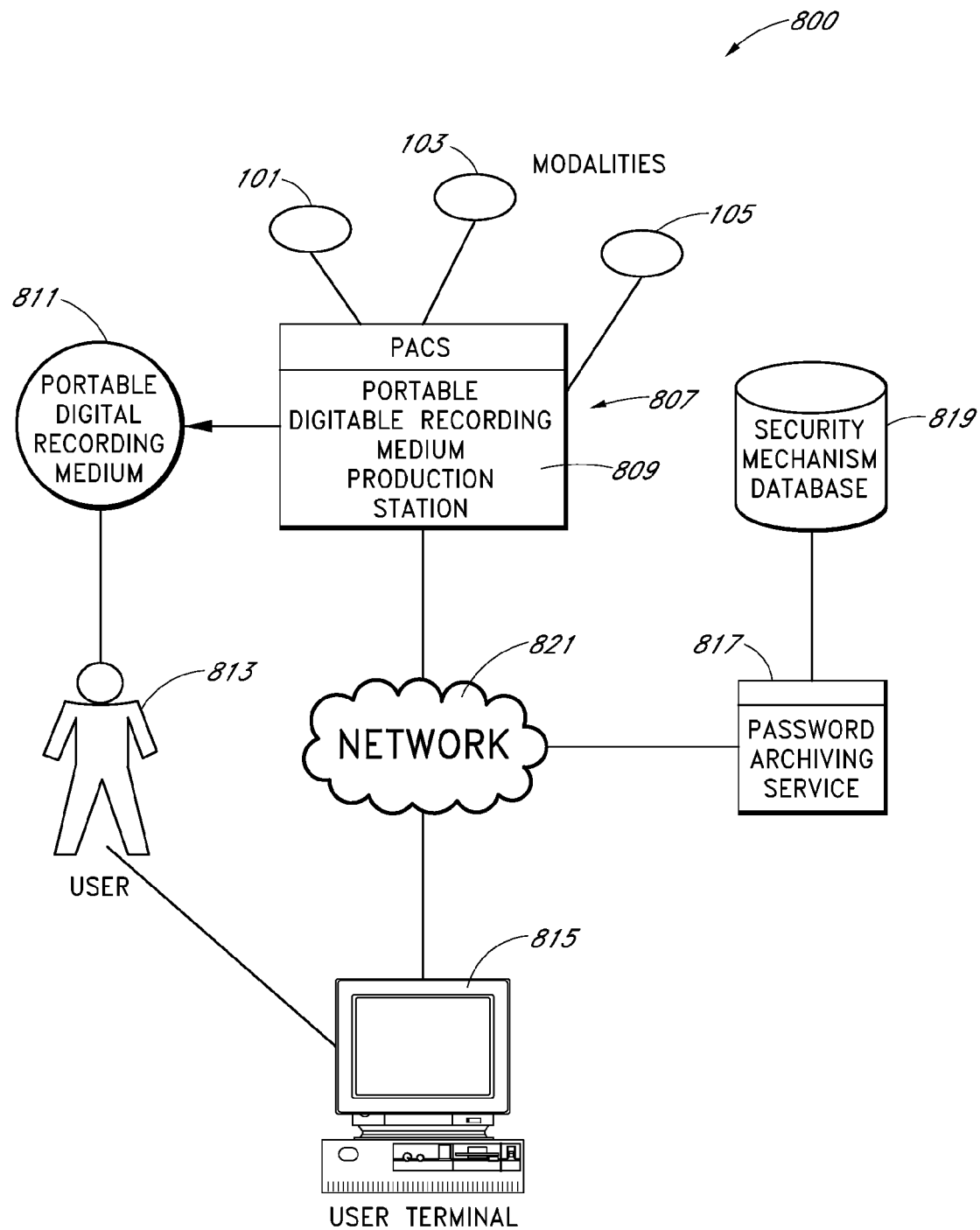
FIG. 8 illustrates a block diagram of another system configured for secure storage and retrieval of DICOM data according to some embodiments.

FIG. 8 illustrates a block diagram of an example system 800 configured for secure storage and retrieval of DICOM data. As shown, the system 800 can include a PACS 807, a portable recording medium 811, a user 813, a user terminal 815, a password archiving and retrieval service 817, and a network 821.

As explained above, the PACS 807 is configured to receive data (e.g., medical data) from various modalities 101, 103, and 105. Modalities can include medical imaging instruments, such as ultrasound, magnetic resonance, PET, computed tomography, endoscopy, mammograms, and HIS and RIS configured to provide patient data, such as medical reports in the HL-7 format.

The PACS 801 can comprise a portable digital recording medium production station 809 configured to record digital data onto the portable medium 811. For example, the portable digital recording medium station 809 can be configured to record software such as a DICOM compliant image viewer onto the medium 111. The software can allow a user to view medical image data on any general purpose computer. An example portable digital recording medium production station is described in U.S. Pat. No. 7,302,164 to Wright et al. (filed on Jan. 17, 2001) (issued on Nov. 27, 2007), which claims priority to Provisional Patent Application Ser. No. 60/181,985 (filed Feb. 11, 2000), both of which are hereby expressly incorporated by reference in their entireties.

The portable digital medium production station 809 is configured to write encrypted medical data to the medium 811. Encrypted medical data can include data such as encrypted DICOM images, encrypted medical reports, and encrypted patient data. The PACS 807 can receive encrypted medical data directly from the modalities 101, 103, and 105 and write this encrypted medical data to the medium 811.

In certain embodiments, the PACS 807 receives unencrypted medical data from the modalities 101, 103, and 105. The PACS 807 subsequently encrypts the medical data before the portable digital medium production station 809 writes the medical data to the medium 811. The PACS 807 can comprise a processor configured to encrypt the medical data using a certificate and/or a public key infrastructure.

The PACS 807 can comprise a processor configured to encrypt the medical data using a password-based encryption mechanism. The password-based encryption methods can be in conformance with the DICOM Part 10 standard and utilize DICOM CMS and PKCS #5 encryption. Of course, other forms of encryption and security mechanisms, such as SHA-1, MD5, RSA, AES, and DES can be employed in the embodiments.

The password can be generated by the PACS 807 randomly or, in certain embodiments, generated based on input by a user. One or more users 813 can optionally be provided with a copy of the password in various ways, such as an e-mail, postal mail, text messaging, etc.

The password can also be generated by and received from a password archiving and retrieval service 817 (described in more detail below) through the network 821. In some embodiments, the password archiving and retrieval service 817 is provided with a copy of the password, preferably in an encrypted form, via the network 819. For example, one or more users 813 can subscribe to password archiving and retrieval service 817, and this subscription can cause PACS 807 to communicate the password to the password archiving and retrieval service 817.

The portable digital medium production station 809 can be configured to write a security mechanism to the medium 811. A security mechanism is a data structure configured to provide access to encrypted data. For example, the security mechanism can be a decryption mechanism. In certain embodiments, the security mechanism can comprise a certificate, a public key infrastructure, or a password, as described above. The security mechanism preferably can be stored in encrypted form on the medium. In certain embodiments, the PACS 807 can comprise a processor configured to encrypt the security mechanism. Alternatively, the PACS 807 can be configured to receive the password in an encrypted form from the password archiving and retrieval service 817 through the network 821.

The password archiving and retrieval service 817 can store a unique decryption key associated with the unique combination of user and medium 811. For example, each medium associated with a user can receive a unique decryption key, which is stored in the security mechanism database 819 associated with the password archiving and retrieval service 817. In certain embodiments, a unique decryption key is associated with every medium. A unique decryption key can advantageously permit the password archiving and retrieval service 817 to authenticate a medium or a unique combination of user and medium. In some embodiments, a unique decryption key is associated with each user and is stored on the medium 811 associated with (e.g., designated for) user.

Medium 811 can be any suitable medium for storing medical images and associated data. For example, medium 811 can include an optical medium such as a CD (e.g., CDROM, CD-R, CD-RW), a DVD (e.g., DVD-ROM, DVD-R, DVD-RAM), or Blu-ray. As another example, the medium 811 can be a portable memory device (e.g., memory stick, USB flash drive, etc.). Those of ordinary skill in the art will understand that any suitable portable digital recording medium can be used in the systems and methods disclosed herein.

A user 813 is any entity that has possession of the medium 811. An example user can be; for example, a patient, a doctor or other medical professional, or an entity such as a hospital or clinic.

A user terminal 815 is any processing device comprising hardware and software capable of accessing the medium 811 and the medium's contents. For example, a user terminal 815 can be a PC having an optical drive configured to read a DVD or a USB drive configured to access a USB flash drive. One skilled in the art will recognize that other types of computing types, such as laptops, servers, mobile phones, etc., can be employed in embodiments of the present disclosure as part of system 800.

A password archiving and retrieval service 817 is a service in communication with the user terminal 815 and/or the PACS 807 via the network 819. Preferably, the password archiving and retrieval service 817 comprises a secure web site interface (e.g., www.dicomdisc.com/password) accessible by a user 813 via the Internet. The password archiving and retrieval service 817 comprises at least one security mechanism database 819 configured to store security mechanism data. The password archiving and retrieval service 817 can further comprise at least one processor configured to provide user services. For example, example services can include generating security mechanism data, such as a password or retrieving password data from the security mechanism database 819.

The password archiving and retrieval service 817 can be configured with at least one user registration database and/or facility registration database configured to store registration data.

For user registration, a user 813 can submit user registration data to the password archiving and retrieval service 817. Example user registration data can include name, date of birth, address information, phone numbers, job title, etc. The password archiving and retrieval service 817 can optionally authenticate the user using proven practices and third party information stores to ensure that the user registration data is authentic and/or authorized.

Upon successful registration, the user 813 can be granted access to the password archiving and retrieval service 817. For instance, the password archiving and retrieval service 817 can assign the user a unique code (e.g., user_id or facility_id) in the user registration database, which can be comprised by the security mechanism database 819.

In some embodiments, a facility having multiple users and user terminals may register as a facility and utilize a facility identifier. Upon the receipt of a facility identifier (such as a facility_id), individual devices (e.g., portable digital recording medium production stations 809) can then be registered for that facility. Information such as product name, product type and end users identifier within the facility can be stored in the database. In addition to this, unique information can be generated automatically from the device to produce a unique registration string, which is described further below. Upon receipt of this information, a unique code can thus be attributed to the device (device_id).

Registration of a device can be performed with the password archiving and retrieval service 817 and a unique registration string known only to the password archiving and retrieval service 817 and the device can be generated. Components that affect this registration string may be characteristics that are unique to the device being registered. For example, these components can include, but are not limited to, the following:

Motherboard serial number;
MAC address;
Random generated mouse co-ordinates/pixel data;
Public/private key;
Timezone;
CPU serial number;
Hard disk serial number;
Etc.

In some embodiments, password archiving and retrieval service 817 may gather this information from the device via communications protocols, such as TCP/IP and Windows Management Interface (WMI). Of course, those skilled in the art will recognize that a wide variety of data and algorithms may be employed in order to develop a unique registration for the device.

For a job submission, upon the receipt of a device_id, a device will attempt to submit a job to the password archiving and retrieval service 817. In some embodiments, a job is the creation of the medium 811 by the portable digital recording medium production station 809. The password archiving and retrieval service 817 may process this request in various ways. For example, the password archiving and retrieval service 817 may check to ensure that the device_id is a current password archiving registered device. In other words, password archiving and retrieval service 817 may check whether a user's or device's subscription to the service remains current or has not expired.

Next, password archiving and retrieval service 817 may check to ensure that the device claiming to use the registered device_id, is the same device that registered initially with the password archiving and retrieval server. The password archiving and retrieval service 817 may employ various techniques, such as hashing algorithms, digital signatures, etc. to authenticate a device and/or the user.

The password archiving and retrieval service 817 may then generate an internal job identification (e.g., job_id) comprising the product, password, and a unique string (e.g., a timestamp). The password archiving and retrieval service 817 may, if required, automatically produce passwords. The password archiving and retrieval service 817 can then return a unique code (e.g., a "NV" number) back to the device.

Registered facilities may authorize a user as being their facility's account managers (FAM). Such managers can run reports of encrypted data usage, registered devices and backup status. FAMs may also be accountable for ensuring that the end users attributed to their facility are still valid and authorized to access encrypted data. For example, every month/week/request, a report from the password archiving and retrieval service 817 can be sent to the FAM showing them the users that they currently have and any requests related to those users. The report may permit the FAM to authorize individual or all end users as remaining current.

Should a facility choose to do so, regular backups, such as daily or weekly, may be uploaded to the password archiving and retrieval service 817. In the event of a device failing, the password archiving and retrieval service 817 will make available these daily backups to a facility's IT staff in order to assist in the replacement of the device.

Figure 9:
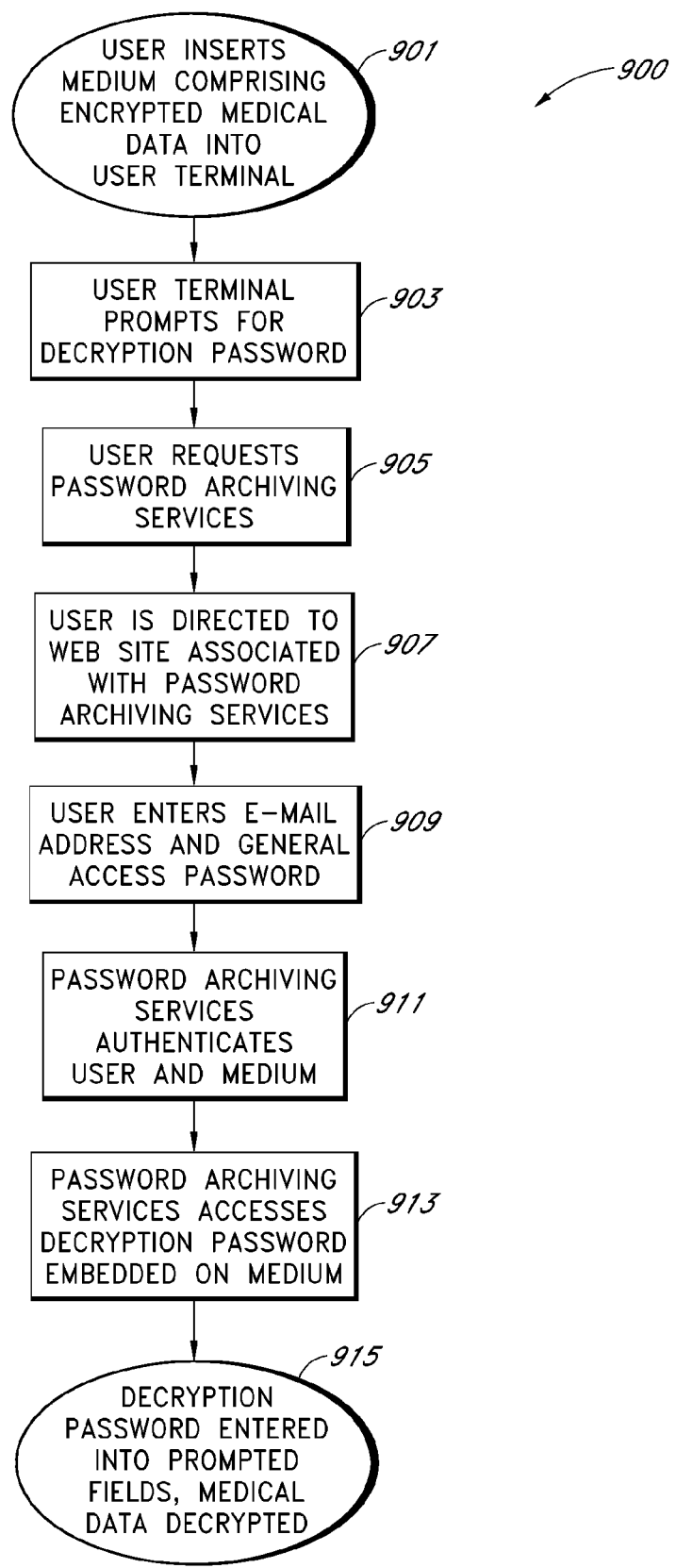
FIG. 9 illustrates a process flow for accessing encrypted DICOM data stored on a portable medium according to some embodiments.

FIG. 9 illustrates a process 900 for accessing encrypted DICOM data stored on a portable medium 811 according to some embodiments. As shown at stage 901, in order to access or view information on the medium 811, the user 813 inserts the medium 811 into the user terminal 815. The user terminal 815 may then determine that the medium 811 contains encrypted information and, optionally, that password archiving and retrieval service 817 can be communicated with if needed. As shown at stage 903, initially, the user 813 can be prompted to provide the password to access encrypted medical data stored on the medium 811.

For example, as explained above, the medium 811 can optionally comprise an embedded DICOM image viewer. In certain embodiments, the embedded DICOM viewer can be configured to recognize the medical data on the medium as being encrypted and prompt the user for the password.

However, the user may not recall or know the decryption (i.e., access) password. For example, the user 813 may have forgotten the password or misplaced it.

Alternatively, the user 813 may be a person other than the original person who received the medium 811. For example, as explained above, the user 813 may be a doctor, nurse, or other medical professional who has been provided the medium 811 as part of treatment of a patient. Accordingly, as shown at stage 905, the user 813 can optionally access a dialog that allows the user 813 to request the services of the password archiving and retrieval service 817. As an example, in the dialog requesting the decryption password, as described above, a button can be provided labeled "Forgot Password" or "Request Password."

In order to access the medium 811, the user 813 may provide certain information that identifies him or her. For example, upon detecting that medium 111 contains encrypted information, the user terminal 815 may read a network location, such as a uniform resource locator (URL) that allows the user terminal 815 to gain access. In response, the user terminal 815 may open a browser window or other application and provide an interface element, such as pop-up window, that prompts the user for some authentication information. The user 813 can then enter an e-mail address, general access password, or other unique credential(s), such as date of birth, an automatically-detected IP address, or information stored on the label of the medium 811.

In the example of FIG. 9, as shown at stage 907, the "Forgot Password" or "Request Password" button opens a web browser on the user terminal 815 directed to a secure web site associated with the password archiving and retrieval service 817. As shown at stage 909, at the web site the user 813 is prompted for an e-mail address and a general access password as login information.

Upon receiving these credentials, the password archiving and retrieval service 817 may be called, for example, via an API or other type of remote communication service. Through this API or service, the credentials can be transmitted to the password archiving and retrieval service 817 via the network 821.

As shown at stage 911, the password archiving and retrieval service 817 will compare the supplied credential to the user registration data and make an authentication decision. If the supplied credential matches the user registration data stored by the password archiving and retrieval service 817, the password archiving and retrieval service 817 may determine a unique decryption key and other types of information about the encrypted information stored on the medium 811. In some embodiments, this can be achieved by analyzing the security mechanism stored on the medium 811.

As shown at stage 913, with this decryption key, the password archiving and retrieval service 817 may access the encrypted password embedded on the medium 811 via the user terminal 115 in communication with the network 821. In some embodiments, this processing is performed automatically or without user intervention.

As an example, the password archiving and retrieval service 817 can determine if the user or machine is listed in the user registration database. If the user is authenticated, the password archiving and retrieval service 817 can then access the unique encrypted password embedded on the medium 811.

As shown at stage 915, the password archiving and retrieval service 817 may then provide the decrypted password to the image viewer in order to allow it to display and view the images. In certain embodiments, the user terminal 815 decrypts the encrypted medical data automatically. In certain embodiments, the user terminal 815 may automatically complete a prompted "password" field. The user 813 may then rely on this provided password to in order to view the encrypted medical data, without necessarily knowing the password. In some embodiments, the password archiving and retrieval service can communicate the password to the user 813 and the password is compared to a password stored in the security mechanism of the medium 811.

Although the present invention has been described with reference to exemplary embodiments, persons skilled in the art will recognize that changes may be made in form and detail without departing from the spirit and scope of the invention. For example, references to a web retrieval site or service made herein will be understood by a skilled artisan to encompass other remote access means such as electronic mail, instant messaging, text messaging, telephone, and the like. Accordingly, the scope of the present invention is defined only by reference to the appended claims.

What is claimed is:

1. A computer-implemented system for providing access to securely stored medical data comprising:
   a database configured to store a decryption password for decrypting encrypted medical data stored on a portable medium, wherein the decryption password is generated from a non-user ID, medically related information identified by a DICOM tag;
   a secure interface configured to authenticate a request for decryption of the encrypted medical data stored on the portable medium; and
   a password retrieval service configured to:
      receive the authenticated request from the secure interface;
      receive non-user ID, medically related information identified by at least one DICOM tag;
      retrieve from the database a decryption password uniquely associated with the encrypted medical data stored on the portable medium, wherein the portable medium is associated with one decryption password;

communicate the decryption password for accessing the encrypted medical data stored on the portable medium;

access a security mechanism stored on the portable medium by comparing the communicated decryption password with a decryption key associated with the portable medium; and when there is a match, transform the encrypted medical data stored on the portable medium into a format accessible by the user, wherein the decryption key is used to decrypt the encrypted medical data into plaintext.

2. The system of claim 1, wherein the secure interface is a secure web interface.

3. The system of claim 1, wherein medical data is represented in Digital Imaging and Communications in Medicine (DICOM) format.

4. The system of claim 1, wherein the non-user ID, medically-related information identified by a DICOM tag comprises the date of a medical exam.

5. The system of claim 1, wherein the non-user ID, medically-related information identified by a DICOM tag comprises the name of a physician.

6. The system of claim 1, wherein the non-user ID, medically-related information identified by a DICOM tag resides within encrypted medical data on the portable medium.

\* \* \* \* \*